United States Patent [19]

Hallowitz et al.

[11] Patent Number: 5,714,390
[45] Date of Patent: Feb. 3, 1998

[54] CARTRIDGE TEST SYSTEM FOR THE COLLECTION AND TESTING OF BLOOD IN A SINGLE STEP

[75] Inventors: Robert A. Hallowitz, Montgomery; Chester F. King, Frederick County, both of Md.

[73] Assignee: Bio-Tech Imaging, Inc., Frederick, Md.

[21] Appl. No.: 732,784

[22] Filed: Oct. 15, 1996

[51] Int. Cl.$^6$ .................................................. G01N 33/553
[52] U.S. Cl. .......................... 436/526; 128/770; 422/55; 422/58; 422/82.05; 435/7.92; 435/7.94; 435/970; 435/975; 436/63; 436/164; 436/800; 436/805; 436/808; 436/824; 604/272; 604/327; 604/411; 604/416; 606/167; 606/181; 606/185
[58] Field of Search .................................. 128/770; 422/55, 422/58, 82.05; 435/7.92, 7.94, 970, 975; 436/518, 526, 63, 164, 800, 805, 808, 824; 604/272, 327, 346, 403, 411, 414, 416; 606/167, 181, 183, 185

[56] References Cited

U.S. PATENT DOCUMENTS

| | | | |
|---|---|---|---|
| 3,203,540 | 8/1965 | Kalt | 206/569 |
| 3,272,319 | 9/1966 | Brewer | 206/569 |
| 4,122,947 | 10/1978 | Falla | 206/569 |
| 4,329,317 | 5/1982 | Detweiler et al. | 422/58 |
| 4,365,970 | 12/1982 | Lawrence | 436/66 |
| 4,382,062 | 5/1983 | Kohl | 422/56 |
| 4,777,964 | 10/1988 | Briggs | 128/760 |
| 4,935,147 | 6/1990 | Ullman | 210/695 |
| 5,054,499 | 10/1991 | Swierczek | 128/770 |
| 5,186,827 | 2/1993 | Liberti | 210/222 |
| 5,201,324 | 4/1993 | Swierczek | 128/770 |
| 5,231,993 | 8/1993 | Haber et al. | 128/770 |
| 5,238,810 | 8/1993 | Fujiwara | 435/5 |

*Primary Examiner*—Susan Wolski
*Attorney, Agent, or Firm*—Millen, White, Zelano & Branigan, P.C.

[57] ABSTRACT

The invention is a device and a method for collecting samples mixing the samples with test reagents, and acting as a container in which the mixture can be incubated and the test reaction viewed by microscope or imaging device. This device enables an entire test to be performed in one simple step without complicated handling procedures. The device consists of a cartridge with a well with micro-lances imbedded in the bottom of the well and an overlying micro-baggy containing a mixture of reagents. There are two reagents present in the micro-baggy: the first consisting of antibodies coupled to paramagnetic microspheres and the second consisting of antibodies coupled with a fluorochrome. A test subject presses down onto the micro-baggy and at the same time punctures his/her finger or thumb on the micro-lances. Once the finger has been lanced, breaking the micro-baggy, the reagents mix with the test subject's blood. The well is then covered by a clear mylar strip. After incubation the cartridge is moved to a viewing platform. A magnetic gradient is applied to the side of the well causing the magnetic separation of antibodies bound to infected peripheral blood lymphocytes from uninfected peripheral blood lymphocytes. A focused light source is applied to the well, causing antibodies bound to infected peripheral blood lymphocytes if any are present, to glow at the specific emmision frequency determined by the specific fluorochome. The test subject can be identified by a bar code strip attached to the cartridge.

14 Claims, 4 Drawing Sheets

CARTRIDGE TEST SYSTEM FOR THE COLLECTION AND TESTING OF BLOOD IN A SINGLE STEP

BACKGROUND

1. Field of Invention

This invention relates to blood collection and diagnostics. More particularly, the invention relates to blood collection and diagnostics utilizing techniques such as magnetic separation and photo detection.

2. Description of Prior Art

The prior art collected blood for testing in multiple steps. The first step was to collect the blood into a suitable container from a puncture wound in the skin of a finger or by venipuncture. Then the blood would have to be placed into a container suitable for transporting or mixing with test reagents. Then reagents would have to be added in a multiple step fashion, interrupted by wash steps. The problem with this approach is multiple steps which are time consuming and require training. In the collection of blood, the prior art is still dealing with the lance and test tube methods.

For example, U.S. Pat. No. 4,777,964 to David Briggs, Kent A. Leger, Brenda Briggs (Oct. 13, 1988) provides a system for whomever wishes to ascertain whether or not he is carrying the AIDS virus to perform a blood sampling and to forward the sample to a lab for the further testing. The kit contains a lance and a tube for collecting the sample and requires the user to seal the tube at the ends with putty. This device and kit is only a means for collecting blood and keeping the sample intact for mailing to a laboratory for further testing. No tests are performed using the appliances provided. In addition, the sample must be transferred to a testing vessel and mixed with the appropriate testing medium. There are a host of other test kits and methods for collection and preparation of specimens. The following patents are of interest with respect to their field:

U.S. Pat. No. 4,382,062 to Kohl (May 3, 1983)

U.S. Pat. No. 4,365,970 to Lawrence, et al. (Dec. 28, 1982)

U.S. Pat. No. 4,122,947 to Falla (Oct. 31, 1978)

U.S. Pat. No. 3,272,319 to Brewer (Sep. 13, 1966)

U.S. Pat. No. 3,203,540 to Kalt, et. al. (Aug. 31, 1965)

None of the above patents provide sample collection, preparation and observation of the immunochemical reaction in the same vessel.

Some test media provide for the performance of the magnetic separation, but do not provide for the reaction to occur in the collection apparatus, nor can the complete test be performed outside a controlled laboratory environment where multiple steps must be performed. U.S. Pat. No. 5,186,827 to Paul A. Liberti, Brian P. Feeley, Dhanesh I. Gohel (Feb. 16, 1993) describes an elaborate magnetic separator for separating magnetic particles form a non-magnetic test medium. The magnetic separator includes a non-magnetic container having a peripheral wall with an internal surface area for receiving the test medium, and magnetic means for generating a magnetic field gradient within the container in which tested material is contained in reaction vessels such as test tubes.

There are also methods that utilize magnetic separation and the use of light sources to identify particles. U.S. Pat. No. 5,238,810 to Koichi Fujiwara, Juichi Noda, Hiroko Misutani, Hiromichi Mizutani (Aug. 23, 1993) provides for such a process; however, as with other magnetic separation methods, this method involves multiple apparatus and steps just to collect and prepare the blood samples for testing. This method also focuses on using one reagent for its test, rather than on a double reagent mixture. It provides for various vessel configurations for performing the reaction, but does not include or contemplate a vessel that has served as reagent storage, blood collection, mixture, incubation and viewing device in one.

SUMMARY OF THE INVENTION

The present invention relates to obtaining a blood sample and mixing it with testing reagents in one step, and in one disposable vessel. The vessel can be incubated and the related results of reaction between the reagents and the blood sample can be viewed and read in the vessel by a Fluorescent microscope without additional processing for quick and accurate testing.

The present invention is directed to blood collection and magnetic separation apparatus and methods in which antibody-coupled magnetic particles and antibody-conjugated flourochromes are use to isolate substances of interest from a non-magnetic test medium by means of high gradient magnetic separation and identification by application of focused light.

The present invention relies upon a unique reaction vessel that serves the multiplicity of purposes as stated above. The prior methods of magnetic separation are different simply because of the incompatibility of reaction vessel infiguration with blood sample collection and single step testing. In addition, most magnetic separation devices do not provide for viewing any further reaction within the vessel.

The current invention provides a self-contained micro-baggy of reagents that is punctured and permitted to mix with the sample of blood at the same time the sample is being collected. Further, the chamber in which the blood is collected, and in which the reagents are mixed with the blood, is also the same chamber or vessel used for incubating the reaction mixture, and further, is the chamber in which magnetic separation of the infected cells, if present, is performed. Finally it also serves as the chamber in which the infected cells, if present, are viewed. There is no equivalent multipurpose chamber such as the present invention that provides for blood collection reagent storage, reagent/blood mixing, reaction incubation, magnetic separation and finally, viewing of any infected cells present.

The Cartridge Antigen Test (CAT) is a device that permits blood collection, reagent mixing with blood, incubation of the mixture, magnetic separation, and viewing of the test results. The device consists of a well slide with micro-lances, a micro-baggy full of reagents, a mylar cover strip, and a bar code for identification purposes.

OBJECTS AND ADVANTAGES

Accordingly, several objects and advantages of our invention are the objective of placing the entire process of stabbing the finger, collecting the blood, treating the blood with test reagents, incubating the text mixture and reading the results form a single device with no transfers, additions, or complicated processes. The operator requires no special training to use the device. This allows for faster, automated testing of the results in remote sites and easy labeling of patient's tests and easy disposal of samples.

Still further objects and advantages will become apparent form a consideration of the ensuring description and accompanying drawings.

DETAILED DESCRIPTION

Figure 1:
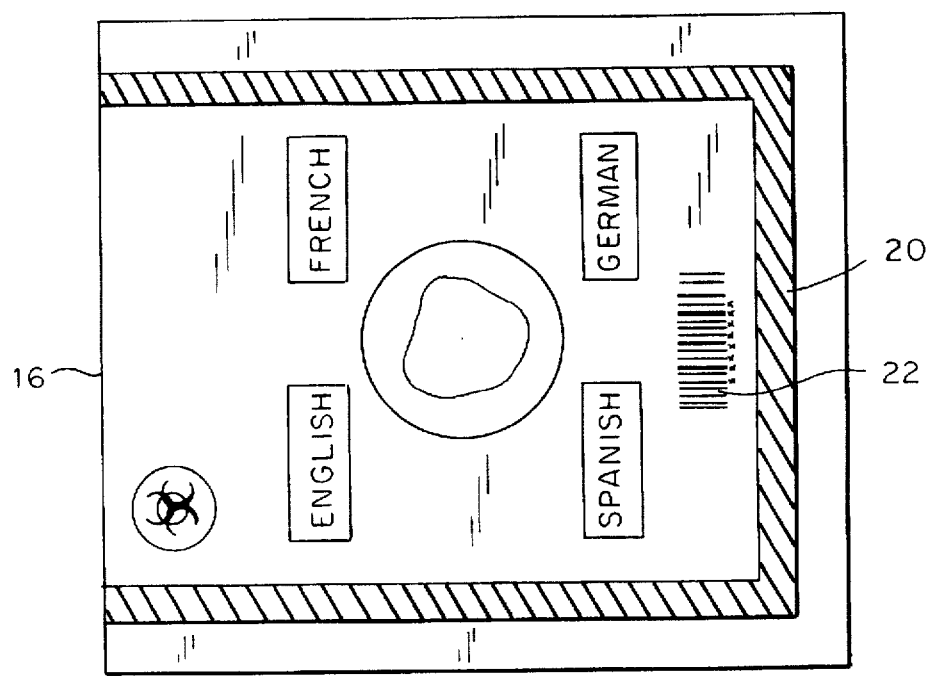
FIG. 1 is a frontal view of a collection/processing cartridge according to the present invention.

FIG. 1 shows the Cartridge Antigen Test (CAT), comprising a cartridge 16 and a clear rectangular piece of plexiglas, ⅜" thick, 2 wide, and 3" long. The well 14, a ¼" deep central hemispherical depression in the middle of the cartridge 16, holds the micro-baggy containing the mixture of reagents 12 and three micro-lances 10. The well 14 is covered by a clear mylar strip 18 and adhesive fastener 20. A bar code strip 22 is near the bottom of the cartridge 16.

Figure 2:
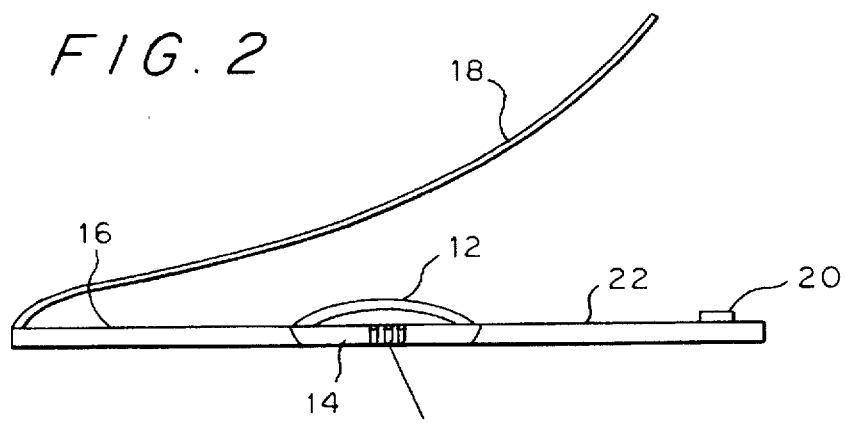
FIG. 2 is a side view of the collection/processing cartridge illustrating a well, micro-lances, a micro-baggy and a mylar cover.

FIG. 2 shows that the well 14 is clear and transparent on the sides, top and bottom, allowing light to pass through the reagent/blood mixture.

Figure 3:
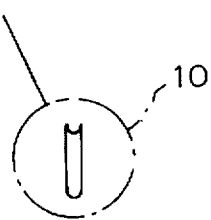
FIG. 3 is an enlarged view of one of the micro-lances shown in FIG. 2.

FIG. 3 shows one of the three micro-lanes 10 which protrude from the bottom of the center of the depression or well 14. Sitting just above the three micro-lances 10 is a micro-baggy containing the mixture of reagents 12.

Figure 4A:
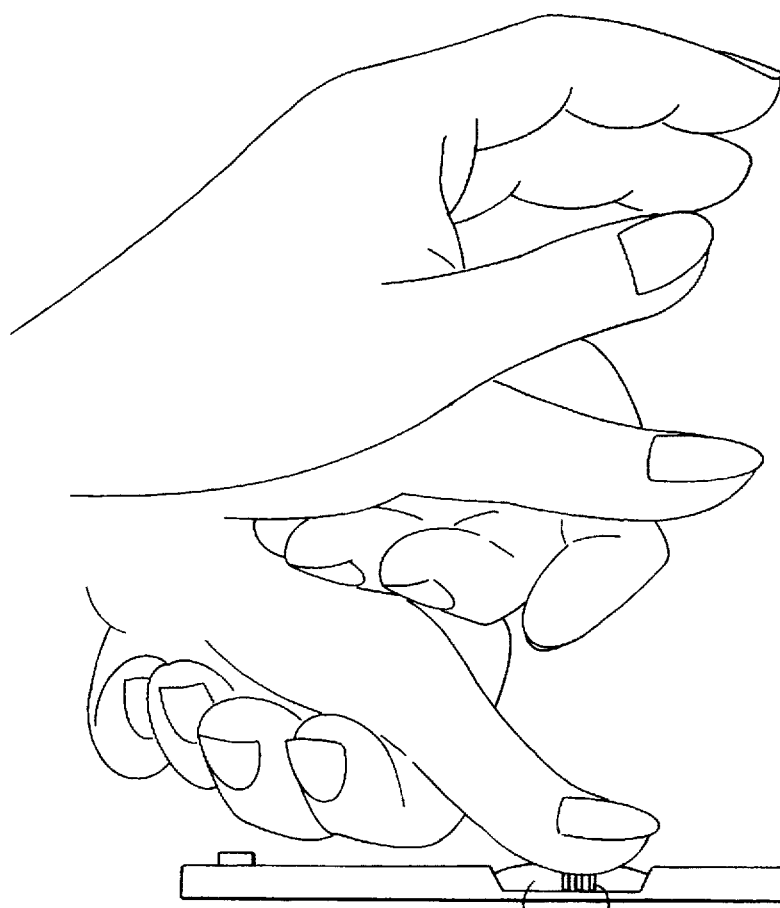
FIGS. 4A–4C are side views illustrating the collection of a blood sample from a test subject.

FIG. 4A shows how a test subject holds his/her hand above the well 14 of the cartridge 16.

Figure 4B:
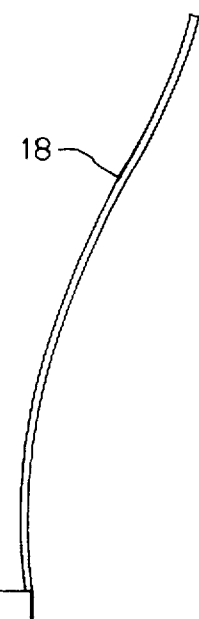
Figure 4C:
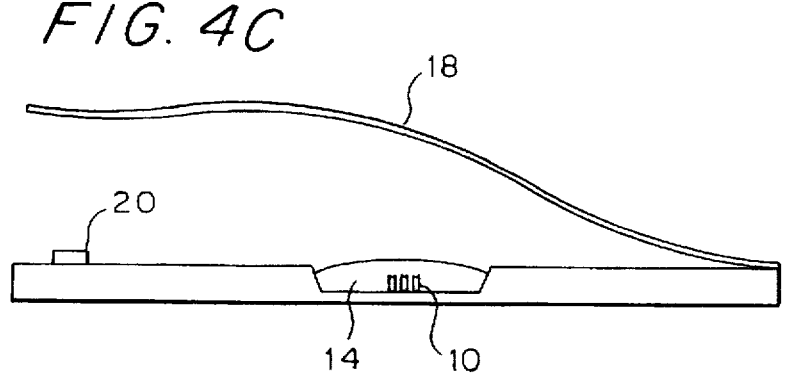

FIG. 4B illustrates how the pressing of the thumb on the micro-baggy containing the mixture of reagents 12 above the three micro-lances 10 will cause the test subject to bleed, the blood to be mixed with the reagents. FIG. 4C shows how the cartridge 16 is sealed after collection with the clear mylar strip 18 by lowering the mylar strip 18 into contact with the adhesive strip 20.

Figure 5A:
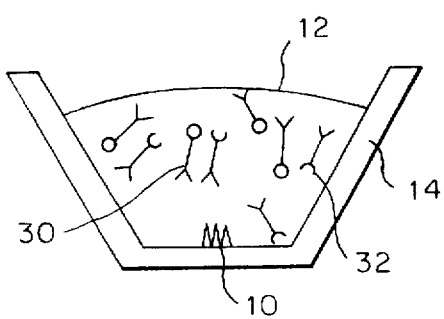
FIGS. 5A–5E are side views of the well and illustrating an immunochemical reaction between blood and a two reagent system including incubation, application of a magnetic gradient, and the application of a focused light source on the reagent and blood mixture.

FIG. 5A is a side view of the well 14 before the test subject bursts the micro-baggy containing the mixture of reagents 12. The well 14 contains two reagents needed for the magnetic separation and fluorescent identification: antibodies coupled to paramagnetic microspheres 30 and antibodies coupled with a fluorochrome 32.

Figure 5C:
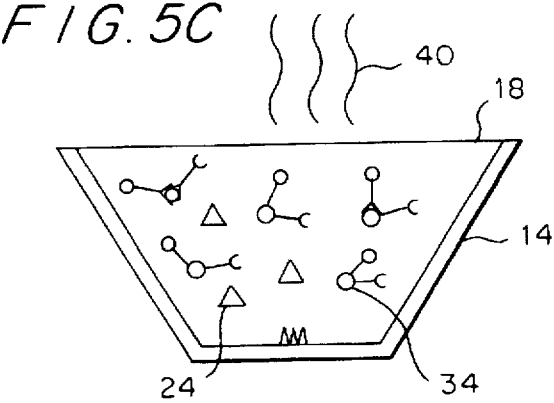
Figure 5B:
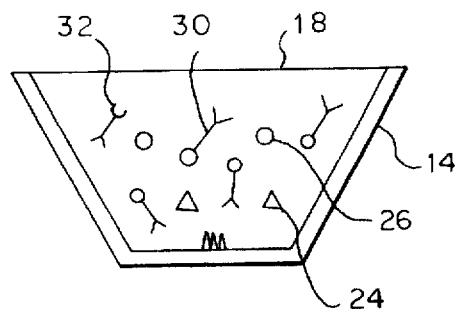

FIG. 5B is a side view of the well 14 covered with the clear mylar strip 18, with the wholl blood sample and reagents prior to incubation.

FIG. 5C is a side view of the well 14 covered with the clear mylar strip 18, after mixing the whole blood sample with the reagents. Incubation 40 is applied to the cartridge 16 and the uninfected peripheral blood lymphocytes 24 remain unaffected by the reagents. The incubation 40 produces antibodies noncompetively bound to infected peripheral blood lymphocytes 34.

Figure 5D:
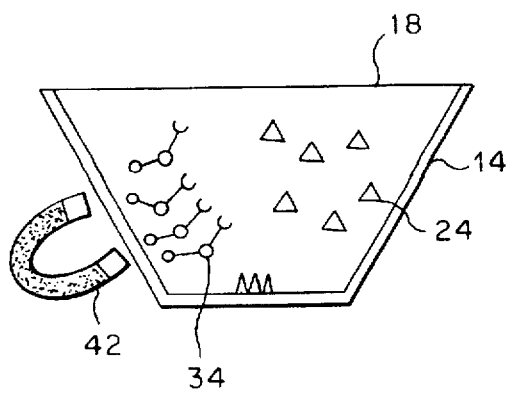

FIG. 5D shows the well 14, being exposed to a strong magnetic gradient 42. The magnetic field caused the migration to the inner surface of the well 14 of all the antibodies noncompetively bound to infected peripheral blood lymphocytes 34 to the point of concentration of the magnetic gradient 42, thus separating the antibodies noncompetively bound to infected peripheral blood lymphocytes 34 from the uninfected peripheral blood lymphocytes 24. The magnetic separation takes approximately 20 seconds.

Figure 5E:
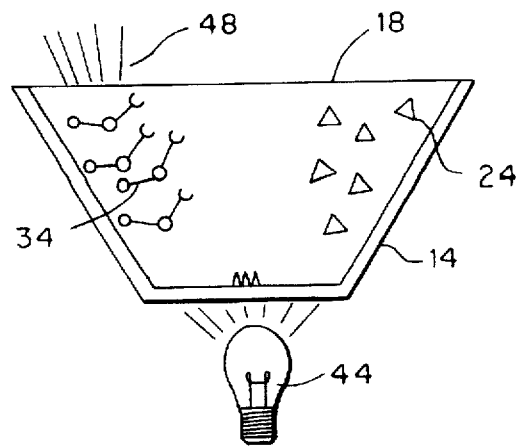

FIG. 5E shows a side view of the well 14 after the magnetic separation has occurred. The predetermined point of maximum magnetic concentration is illuminated by a suitable focused light source 44, for example, at 488 nm wavelength, for FICT, causing all antibodies noncompetively bound to infected peripheral blood lymphocytes 34 now aggregated at the predetermined point to glow 48 at between 520–540 nm fluorescent light. The reaction can then be viewed through a microscope or lens of an imaging system.

Figure 6A:
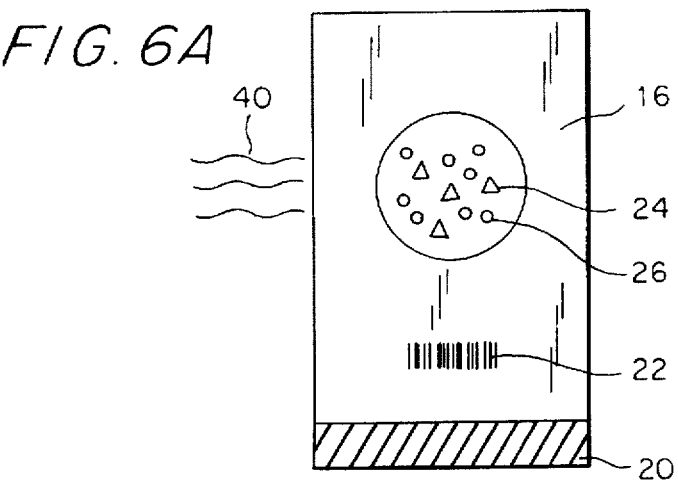
FIGS. 6A–6C are top and side views respectively, of the cartridge and well illustrating incubation, the application of a magnetic gradient and a focused light source, and the observation of the reaction through a lens.
Figure 6B:
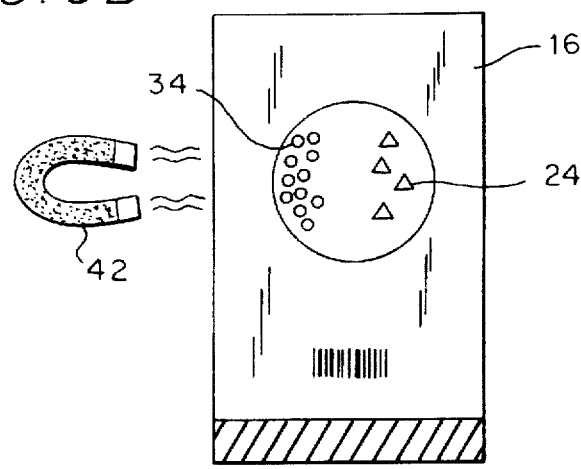

FIG. 6A shows a stop surface view of the cartridge 16. FIG. 6B shows the antibodies noncompetively bound to infected blood lymphocytes 34 being separated from the uninfected peripheral blood lymphocytes 24 by the magnetic field to the concentration pont of the magnetic gradient 24.

Figure 6C:
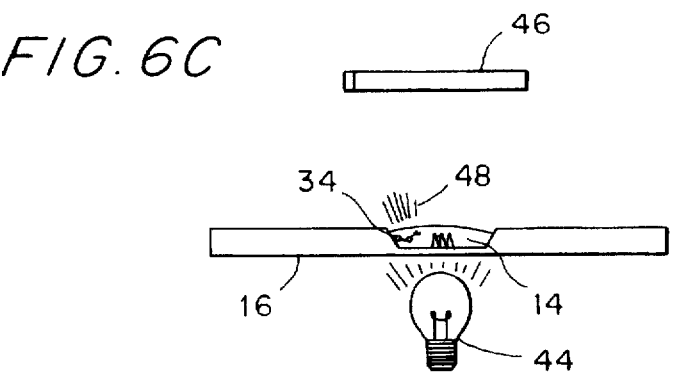

FIG. 6C is a side view of the cartridge 16 and shows how the focused light source 44 is directed through the bottom of the well 14 and the lens 46 placed above the well 14 to view the glow 48 from the reaction.

PREFERRED EMBODIMENT—OPERATION

To use the invention, a test subject presses his/her thumb or finger down onto the micro-baggy containing the mixture of reagents 12 on the CAT. The micro-baggy containing the mixture of reagents 12 bursts. The three micro-lances 10 puncture the thumb or finger causing the individual to bleed. The reagents in the bubble and the blood mix. The clear mylar strip 18 is pulled down and fastened by adhesive fastener 20, sealing the well 14 containing the blood and the reagents.

In the specific embodiment, two reagents must be present in the well to complete both the magnetic separation of the targeted micro-organism and the fluorescent identification of their presence: the first reagent must comprise anti-bodies coupled to paramagnetic microspheres 30 and the second must consist of anti-bodies coupled with a Fluorochrome 32. Both reagents will bind themselves to the infected or target antigen-coated cells during the incubation 40.

The mixture in the sealed cartridge 16 is incubated for 3 to 5 minutes at 37 degrees Centigrade. The cartridge 16 is then moved to a viewing platform. A strong magnetic gradient 42 is applied to the side of the well 14. The magnetic field causes the target antibodies, noncompetively bound to infected peripheral blood lymphocytes 34, to separate from the other untargeted cells to a fixed point where the magnetic gradient 42 is concentrated. A forced light source 44, measuring 488 nm is passed through well 14 and the blood and reagent mixture. The focused light source 44 causes antibodies noncompetively bound to infected peripheral blood lymphocytes 34 to glow 48 at the specific emmision frequency determined by the specific fluorochrome. The reaction can be viewed through a lens 46 or predetermined coordinates of the magnetic gradient 42 with the highest concentration at the inner surface of the well 14 where the antibodies noncompetively bound to infected peripheral blood lymphocytes 34 will be located. If there is no glow then the result is negative, and if there is a glow 48 the result is positive.

The test subject is identified by the bar code strip 22 attached to the cartridge 16.

CONCLUSIONS AND RAMIFICATIONS

Accordingly, it can be seen that the invention simplifies the procedures of blood collection, reagent mixing, patient tracking and test reading by unifying all steps into one functional unit. The positioning of the micro-baggy containing the mixture of reagents 12 above the three micro-lanes 10 allows for blood collection and mixing with the reagents in one step. The clear mylar strip 18 is used to cover the exposed well 14 and the cartridge 16 is incubated 40 at 37 degrees Centigrade.

The invention works with two reagents. The first reagent consists of antibodies coupled to paramagnetic microspheres 30 so that the infected peripheral blood lymphocytes 26 can be separated from uninfected peripheral blood lymphocytes 24 by applying a magnetic gradient 42. The magnetic field generated by the magnetic gradient 42 will cause the antibodies coupled to paramagnetic microspheres 30 attached to the infected peripheral blood lymphocytes 26 to be drawn to a predetermined location of the interior wall of the well 14.

The second reagent consists of antibodies coupled with a fluorochrome 32 so that the infected peripheral blood lymphocytes 26 can be identified if present by applying a focused light source 44 on the well 14 causing the infected peripheral blood lymphocytes 26 to glow at the specific emission frequency determined by the specific fluorochrome. The well 14, covered with a clear mylar strip 18, allows the cartridge 16 to move around and allows the test reaction to be viewed through a lens 46.

LIST OF REFERENCE NUMERALS

10 Three micro-lanes
12 Micro-bag containing the mixture of reagents
14 Well
16 Cartridge
18 Clear mylar strip
20 Adhesive fastener
22 Bar code strip
24 Uninfected peripheral blood lymphocytes
26 Infected peripheral blood lymphocytes
30 Antibodies coupled to paramagnetic microspheres
32 Antibodies coupled with a Fluorochrome
34 Antibodies noncompetively bound to infected peripheral blood lymphocytes
40 Incubation
42 Magnetic gradient
44 Focused light source
46 Lens
48 Glow

SCOPE

Although the description above contains many specificities, these should not be construed as limiting the scope of the invention, but as merely providing illustrations of some of the presently preferred embodiments of this invention. Various other embodiments and ramifications are possible within its scope. For example, a variety of immunochemical reactions used in diagnosing infectious diseases can be done using a cartridge 16, by substituting the reagents in the micro-baggy containing the mixture of reagents 12. An automated cartridge processor can use the CAT to perform test outside of the environment of a high tech laboratory and can be operated by an untrained personnel. Tests that do not require magnetic separation can be performed using this invention.

Thus, the scope of this invention is determined only by the appended claims and their legal equivalents, rather than by the examples given.

We claim:

1. A cartridge antigen test system for collection and testing of a blood sample from a subject in a single step, comprising:

a) a collection/processing cartridge having a well with a bottom, said well comprising a depression in said cartridge, for collection of said blood sample, wherein said bottom of said well is transparent to allow passage of light;

b) at least one lance disposed on said bottom of said well for piercing said subject to collect said blood sample;

c) a baggy containing a reagent or reagents disposed above said at least one lance to allow release of said reagent or reagents when said subject is pierced by said at least one lance; and d) a clear covering material attached to an end of said cartridge for coveting said well.

2. The cartridge antigen test system of claim 1, further comprising an adhesive fastener, at an end of said cartridge opposite to said end where said coveting material is attached, for sealing said covering material over said well after collection of said blood sample.

3. The cartridge antigen test system of claim 1, further comprising a bar code for identification.

4. The cartridge antigen test system of claim 1, further comprising a light source for detection of said reagent or reagents.

5. The cartridge antigen test system of claim 1, wherein said reagent or reagents comprise i) antibodies coupled to magnetic or paramagnetic particles and ii) antibodies conjugated to a fluorochrome, wherein each of said antibodies binds to a test substance of interest.

6. The cartridge antigen test system of claim 1, wherein said reagent or reagents comprise multiple pairs of i) antibodies coupled to magnetic or paramagnetic particles and ii) antibodies conjugated to a fluorochrome, wherein each of said multiple pairs of antibodies binds to one of multiple test substances of interest.

7. The cartridge antigen test system of claims 5 or 6, further comprising a means for producing a magnetic field for magnetically separating said magnetic or paramagnetic particles.

8. The cartridge antigen test system of claim 1, wherein said reagent or reagents comprise i) a capture antigen coupled to latex particles and ii) anti-immunoglobulin conjugated to a fluorochrome, wherein each of said capture antigen and said anti-immunoglobulin bind to an antibody of interest.

9. The cartridge antigen test system of claim 1, wherein said reagent or reagents comprise multiple pairs of i) capture antigen coupled to latex particles and ii) anti-immunoglobulin conjugated to a fluorochrome, wherein each of said multiple pairs of capture antigen and anti-immunoglobulin binds to one of multiple antibodies of interest.

10. A method for collection and testing of a blood sample from a subject for a test substance of interest in a single step using the cartridge antigen test system of claim 1, comprising:

a) pressing a thumb or finger of said subject onto said baggy and said at least one lance to draw blood from said subject into said well and release said reagent or reagents from said baggy into said well;

b) covering said well with said clear covering material;

c) incubating said sample and said reagent or reagents to allow reaction of said sample with said reagent or reagents to produce a signal indicative of said test substance of interest;

d) observing said well for said signal to thereby determine said test substance of interest.

11. The method of claim 10, wherein said reagent or reagents comprise i) antibodies coupled to magnetic or paramagnetic particles and ii) antibodies conjugated to a fluorochrome, and wherein each of said antibodies binds to a test substance of interest, and said method further comprises producing a magnetic field to magnetically separate said magnetic or paramagnetic particles, and applying a light source for determination of said fluorochrome and consequently said test substance of interest.

12. The method of claim 10, wherein said reagent or reagents comprise multiple pairs of i) antibodies coupled to magnetic or paramagnetic particles and ii) antibodies conjugated to a fluorochrome, and wherein each of said multiple pairs of antibodies binds to one of multiple test substances of interest, and said method further comprises producing a magnetic field to magnetically separate said magnetic or paramagnetic particles, and applying a light source for determination of said fluorochrome and consequently said multiple test substances of interest.

13. The method of claim 10, wherein said reagent or reagents comprise i) a capture antigen coupled to latex particles and ii) anti-immunoglobulin conjugated to a fluorochrome, and wherein each of said capture antigen and said anti-immunoglobulin binds to a test substance of interest, and said method further comprises applying a light source for determination of said fluorochrome and consequently said test substance of interest.

14. The method of claim 10, wherein said reagent or reagents comprise multiple pairs of i) capture antigen coupled to latex particles and ii) anti-immunoglobulin conjugated to a fluorochrome, and wherein each of said multiple pairs of said capture antigen and said anti-immunoglobulin binds to one of multiple test substances of interest, and said method further comprises applying a light source for determination of said fluorochrome and consequently said multiple test substances of interest.

* * * * *